(12) United States Patent
Bartlett

(10) Patent No.: US 10,765,535 B2
(45) Date of Patent: Sep. 8, 2020

(54) COMPACT LIMB PROSTHESIS SYSTEM AND METHOD

(71) Applicant: Brian Bartlett, Seattle, WA (US)

(72) Inventor: Brian Bartlett, Seattle, WA (US)

( * ) Notice: Subject to any disclaimer, the term of this patent is extended or adjusted under 35 U.S.C. 154(b) by 126 days.

(21) Appl. No.: 16/122,848

(22) Filed: Sep. 5, 2018

(65) Prior Publication Data

US 2019/0070020 A1    Mar. 7, 2019

Related U.S. Application Data

(63) Continuation-in-part of application No. 14/470,905, filed on Aug. 27, 2014, now Pat. No. 10,182,926, which is a continuation-in-part of application No. 12/925,997, filed on Nov. 4, 2010, now Pat. No. 9,895,269, which is a continuation-in-part of application No. 11/241,831, filed on Sep. 30, 2005, now Pat. No. 7,828,856.

(60) Provisional application No. 62/554,436, filed on Sep. 5, 2017, provisional application No. 60/614,859, filed on Sep. 30, 2004.

(51) Int. Cl.
*A61F 2/64* (2006.01)
*A61F 2/68* (2006.01)
*A61F 2/50* (2006.01)

(52) U.S. Cl.
CPC .................. *A61F 2/64* (2013.01); *A61F 2/68* (2013.01); *A61F 2002/5003* (2013.01); *A61F 2002/503* (2013.01); *A61F 2002/5007* (2013.01); *A61F 2002/5009* (2013.01); *A61F 2002/5033* (2013.01); *A61F 2002/5038* (2013.01); *A61F 2002/6854* (2013.01)

(58) Field of Classification Search
CPC .................. A61F 2/64; A61F 2002/503; A61F 2002/5009; A61F 5/0123; A61F 5/0125
See application file for complete search history.

(56) References Cited

U.S. PATENT DOCUMENTS

| | | | | |
|---|---|---|---|---|
| 9,358,147 B1* | 6/2016 | Ancinec | ................ | A61F 5/0125 |
| 10,182,926 B2* | 1/2019 | Bartlett | .................... | A61F 2/642 |
| 2013/0268093 A1* | 10/2013 | Gilbert | .................... | A61F 2/605 |
| | | | | 623/46 |
| 2018/0280163 A1* | 10/2018 | Dietl | ...................... | A61F 2/605 |
| 2019/0070020 A1* | 3/2019 | Bartlett | ..................... | A61F 2/64 |

* cited by examiner

*Primary Examiner* — Bruce E Snow
(74) *Attorney, Agent, or Firm* — Charles J. Rupnick Attorney at Law

(57) ABSTRACT

A prosthesis system can have an advantageous use over conventional prostheses in certain activities, including, but not limited to certain sports activities: The system includes, elastic member(s) that can store and release energy. The storing and releasing of energy in the elastic members happens during the movements made by the user and with the application of the user's own body weight while performing an activity. Implementations can also include a variety of routing configurations for the elastic member(s), as well as a variety of mounting points to integrate the elastic member(s) into the system, and/or a variety of adjustable anti-hyperextension members, and/or a variety of interchangeable shoes used for applicable activities.

20 Claims, 11 Drawing Sheets

COMPACT LIMB PROSTHESIS SYSTEM AND METHOD

This application claims priority of U.S. Provisional patent application Ser. No. 62/554,436 filed in the name of the same Brian Bartlett on Sep. 5, 2017, the complete disclosure and teachings of which are incorporated herein by reference, and is a Continuation-in-part and claims priority benefit of parent of parent U.S. patent application Ser. No. 14/470,905 filed in the name of Brian Bartlett on Aug. 27, 2014, which is a Continuation-in-part of parent U.S. patent application Ser. No. 12/925,997 filed in the name of the same Brian Bartlett on Nov. 4, 2010, which claims priority benefit of parent U.S. patent application Ser. No. 11/241,831 filed in the name of the same Brian Bartlett on Sep. 30, 2005, now allowed, the complete disclosures and teachings of which are incorporated herein by reference.

FIELD OF THE INVENTION

The present invention relates generally to prosthesis systems.

BACKGROUND OF THE INVENTION

Conventional prosthesis systems can be difficult to use for various activities including some involving certain sports.

SUMMARY OF THE INVENTION

The present invention is a prosthesis system for a human limb that allows for energy to be stored and released via one or more elastic member(s) for many activities, including, but not limited to sports activities such as bicycling, surfing, wakeboarding, snowboarding, downhill skiing, cross country skiing, and waterskiing.

A method of making and operating the prosthesis system is detailed herein.

Other aspects of the invention are detailed herein.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF PREFERRED EMBODIMENT

Figure 1:
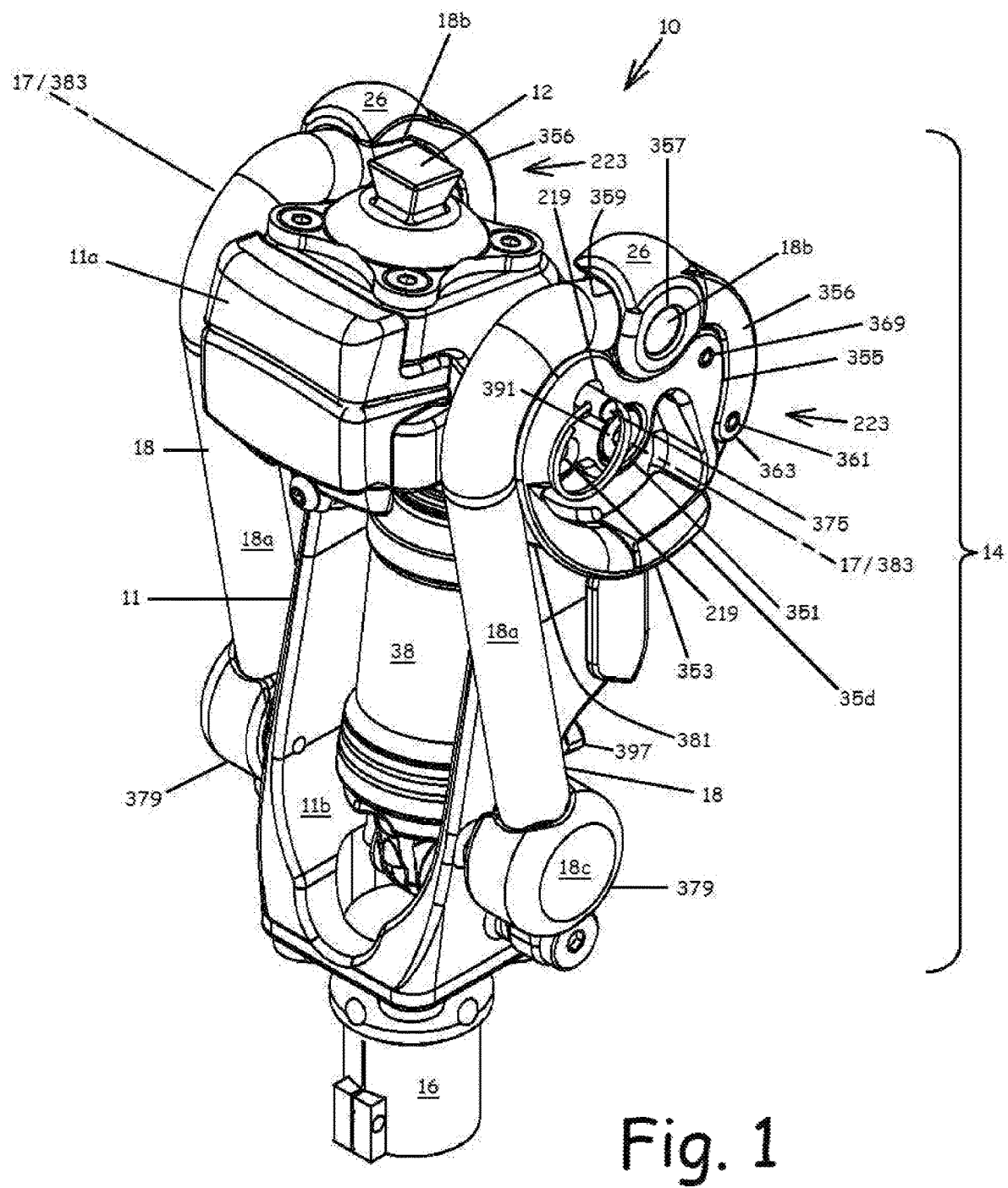
FIG. 1 is a front isometric view of an implementation of a prosthesis system shown in the resting position, having two elastic members routed through a rotational cam member mounted on the knee frame, and shown with an elastic strap acting as a resilient restoring and anti-hyperextension member.
Figure 2:
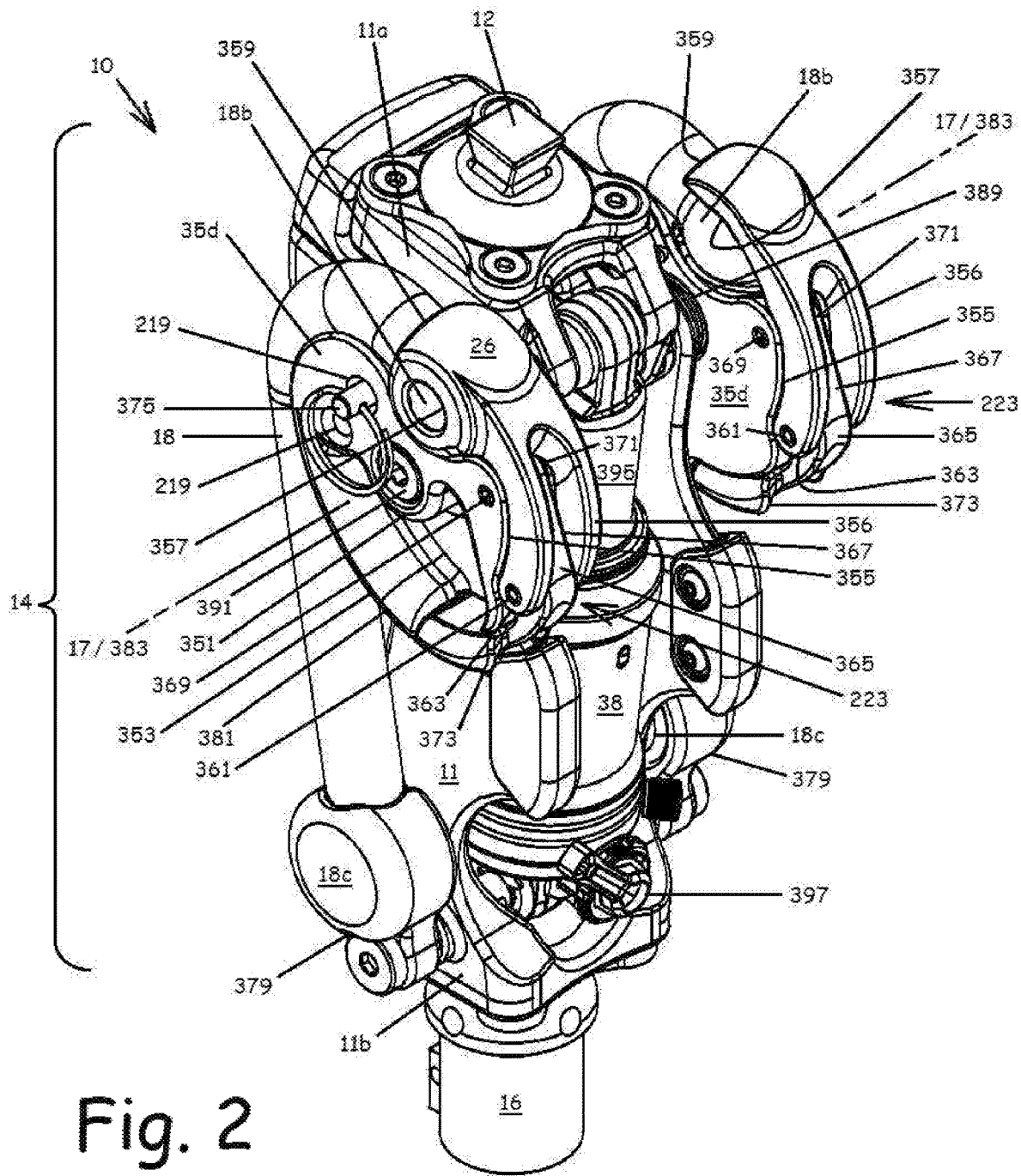
FIG. 2 is a rear isometric view of the prosthesis system shown in FIG. 1.
Figure 3:
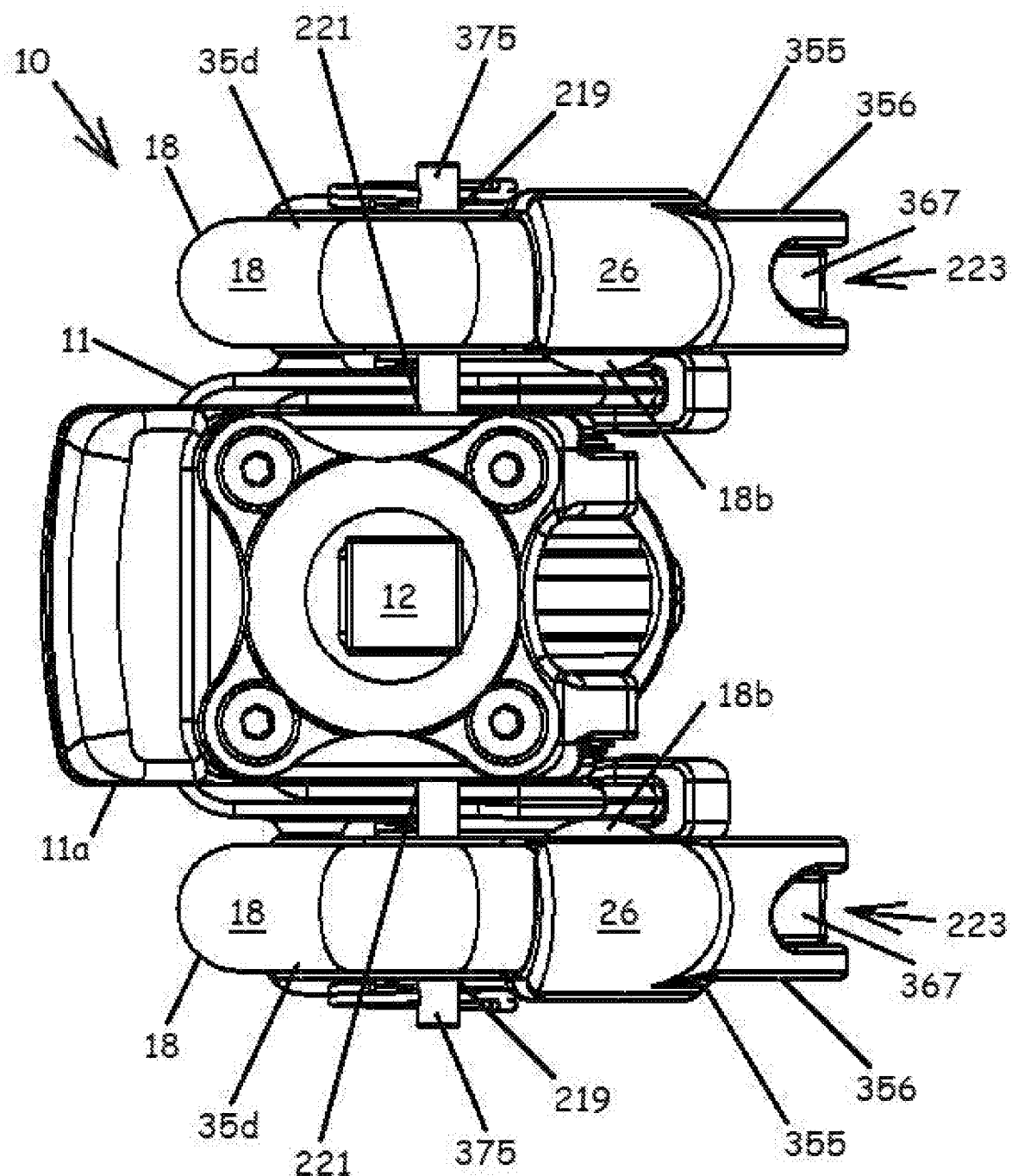
FIG. 3 is a top view of the prosthesis system shown in FIG. 1.
Figure 4:
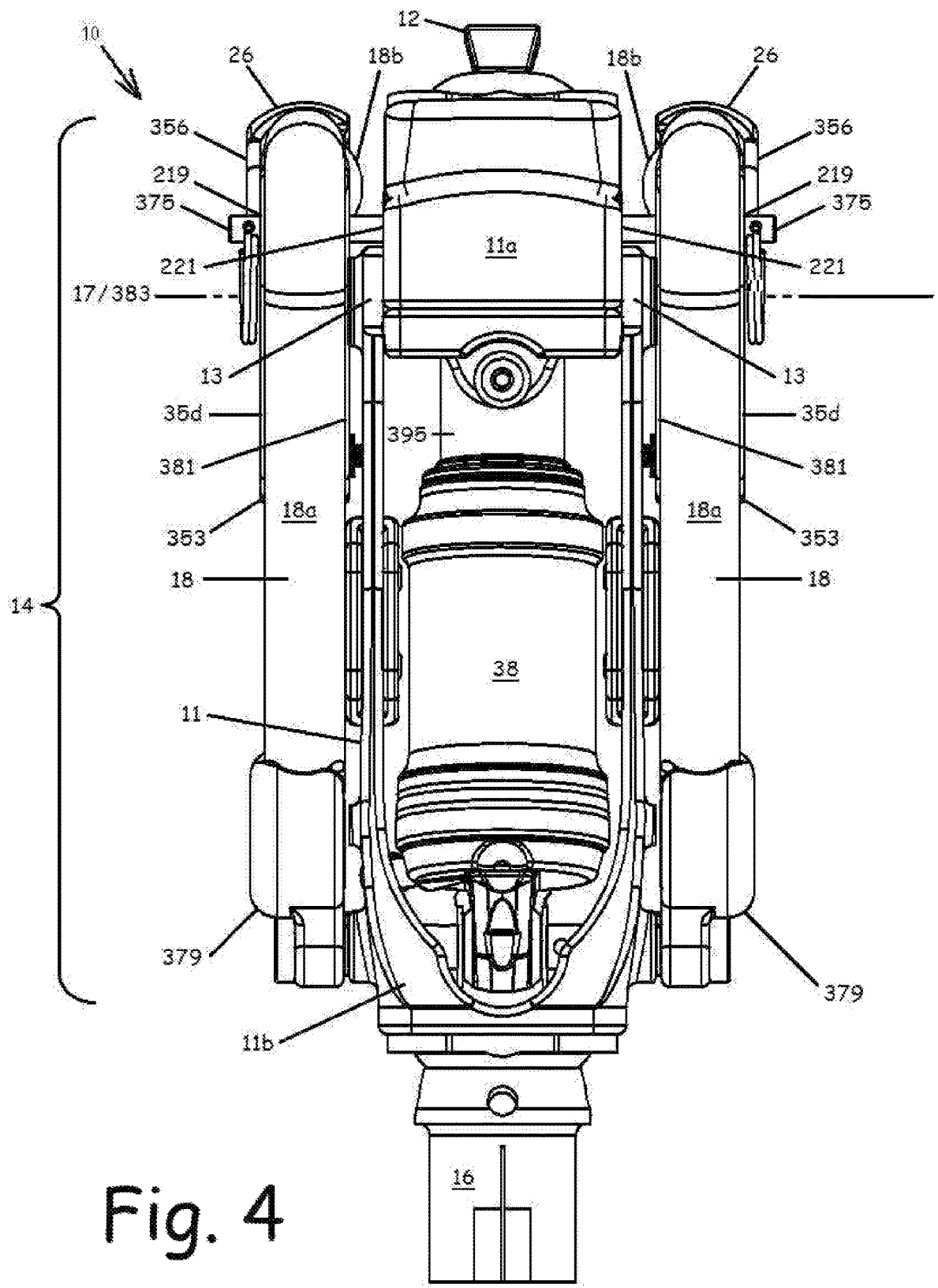
FIG. 4 is a front view of the prosthesis system shown in FIG. 1.
Figure 5:
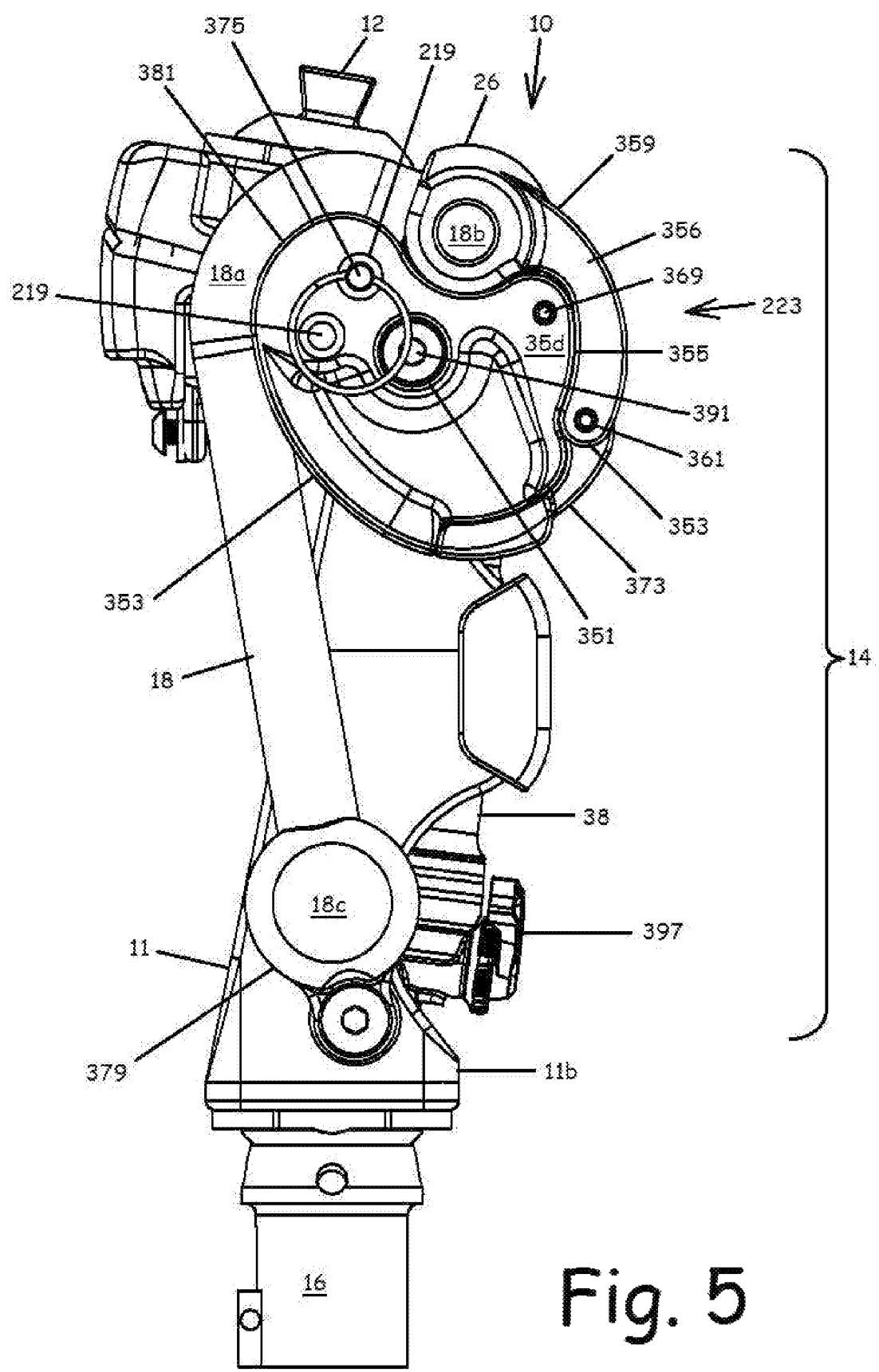
FIG. 5 is a first side view of the prosthesis system shown in FIG. 1.
Figure 6:
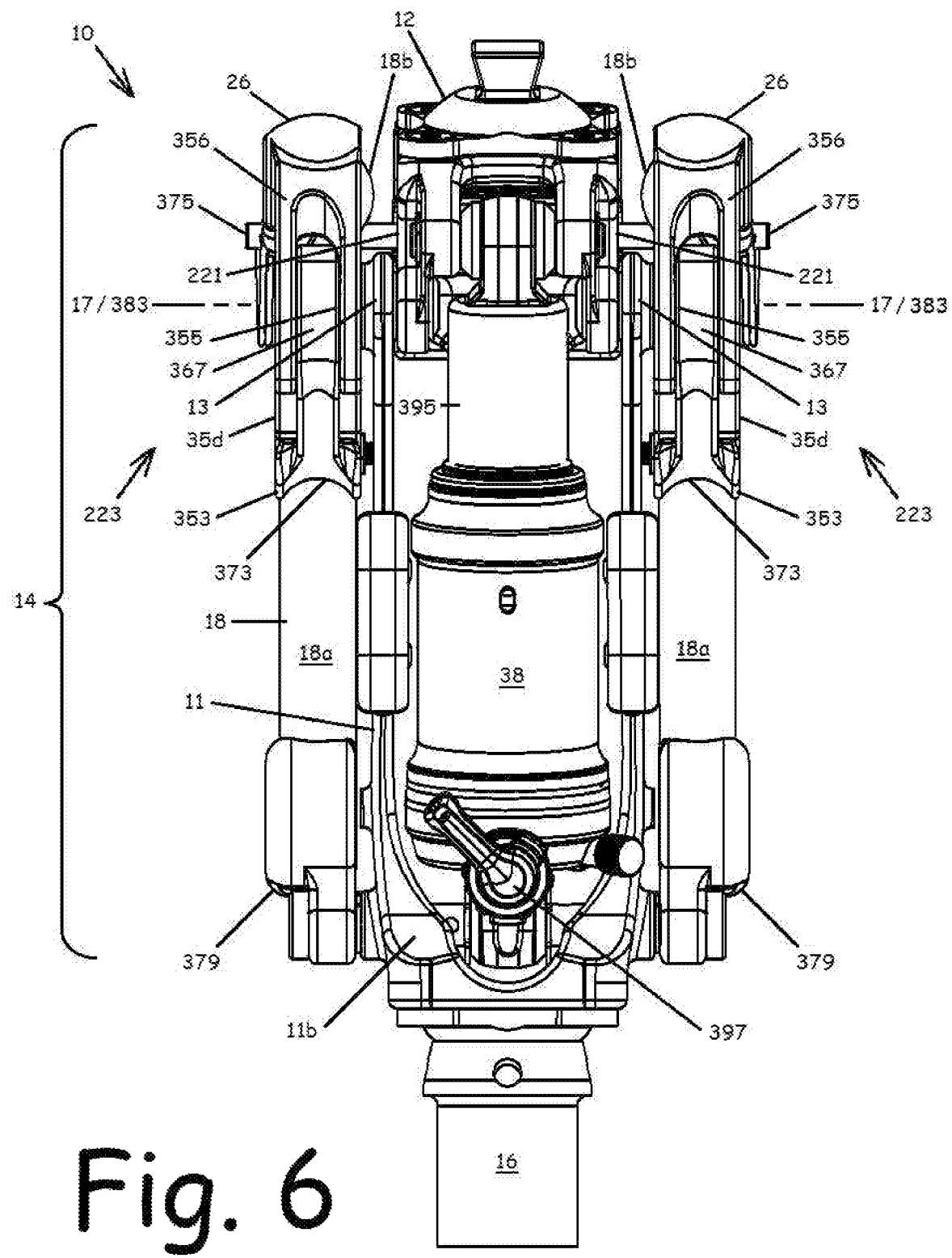
FIG. 6 is a rear view of the prosthesis system shown in FIG. 1.

As required, a detailed illustrative embodiment of the present prosthesis system and method is disclosed herein. However, techniques, systems and operating structures in accordance with the present prosthesis system and method may be embodied in a wide variety of forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein which define the scope of the present prosthesis system and method. The following presents a detailed description of an illustrative embodiment (as well as some alternative embodiments) of the present prosthesis system and method.

In the Figures, like numerals indicate like elements.

A prosthesis system described herein allows for energy to be stored and released via one or more elastic member(s). Based upon this approach potential exists for performance advantages over a conventional prosthesis, such as when used in activities requiring the use muscles such as extensor muscles, for instance, the quadriceps. Present implementations can have an advantageous use over conventional prostheses in many activities, including, but not limited to sports activities such as bicycling, surfing, wakeboarding, snowboarding, downhill skiing, cross country skiing, and waterskiing. The system includes, elastic member(s) that can store and release energy. The storing and releasing of energy in the elastic members happens during the movements made by the user and with the application of the user's own body weight while performing an activity. Implementations can also include a variety routing configurations for the elastic member(s), as well as a variety of mounting points to integrate the elastic member(s) into the system, and/or a variety of adjustable anti-hyperextension members, and/or a variety of interchangeable shoes used for applicable activities.

Represented herein is a novel prosthesis system 10 comprised of an upper human interface portion 12, a compact self-contained joint portion 14, and a lower prosthetic interface portion 16. Included in self-contained joint portion 14 is one or more elastic member(s) 18 (two shown) for storing and releasing energy, and an adjustable anti-hyperextension member 38 that prevents elastic cord members 18 from hyper extending the system. Prosthesis system 10 may also include a foot or other artificial prosthetic appendage (shown by example and without limitation as item 48 in U.S. patent application Ser. No. 14/470,905 the entirety of which is incorporated herein by reference) coupled to the lower interface portion 16, which may be changed accordingly to accommodate any various activities in which the user may wish to engage.

Accordingly, novel compact self-contained joint portion 14 for a human prosthesis limb system 10 includes a hinged frame 11 including a hinge 13 between an upper or proximate frame member 11a and a distal or lower frame member 11b, and a rotatable cam member 35d, and one or more of elastic member(s) 18.

Frame 11 is coupled to upper human interface portion 12 proximate to the user and configured for coupling with the remainder of the user's human limb closer to the user's body than the previous location of the missing joint, and lower artificial prosthetic appendage interface portion 16 positioned distal from the user and configured for coupling with foot or other artificial prosthetic appendage 48 that is intended to replace the user's missing human limb normally residing beyond the missing joint distal from the user's body.

Figure 7:
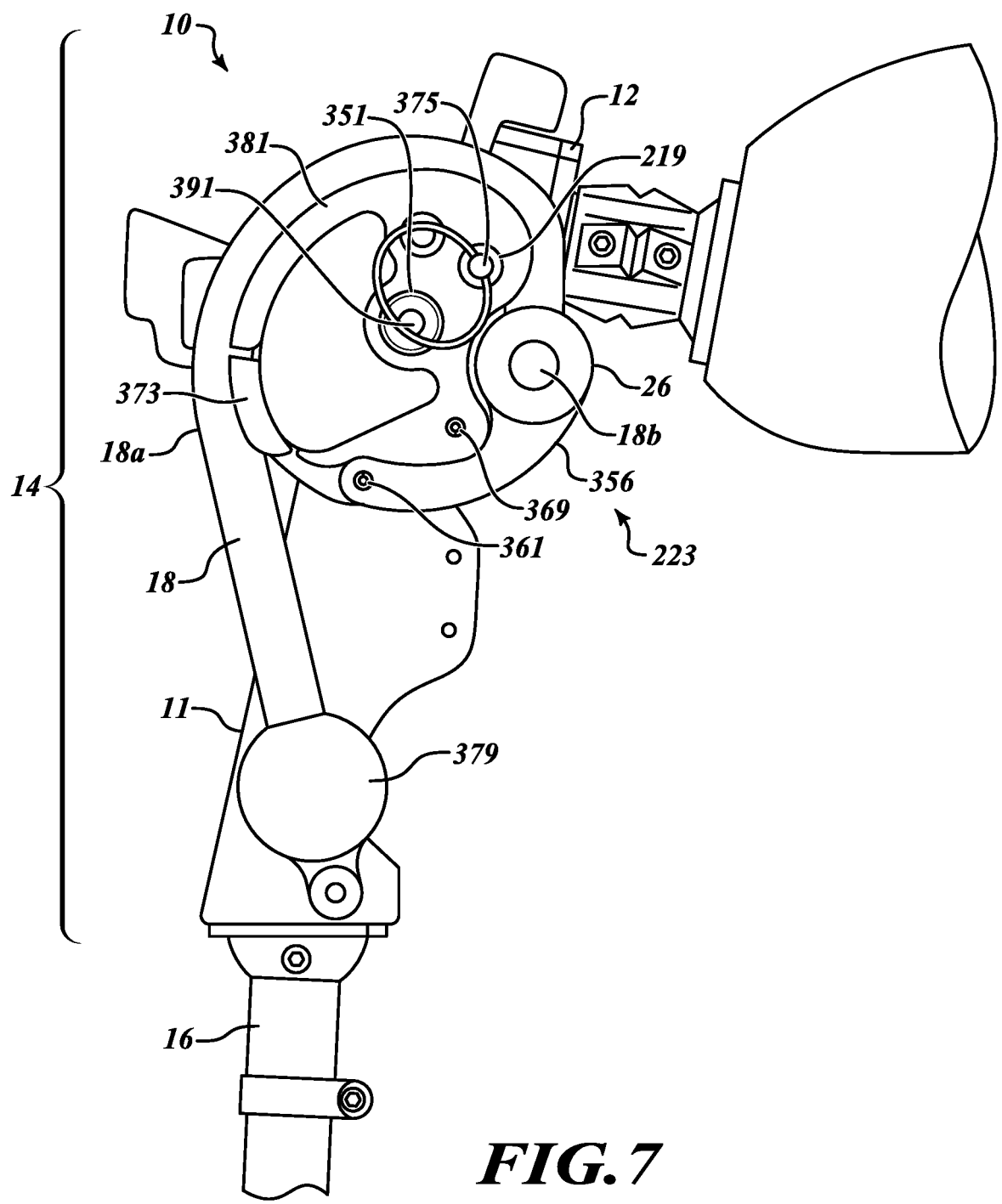
FIG. 7 is a another side view of the prosthesis system shown in FIG. 1 in a bent state having an upper portion rotated relative to a lower portion thereof.
Figure 8:
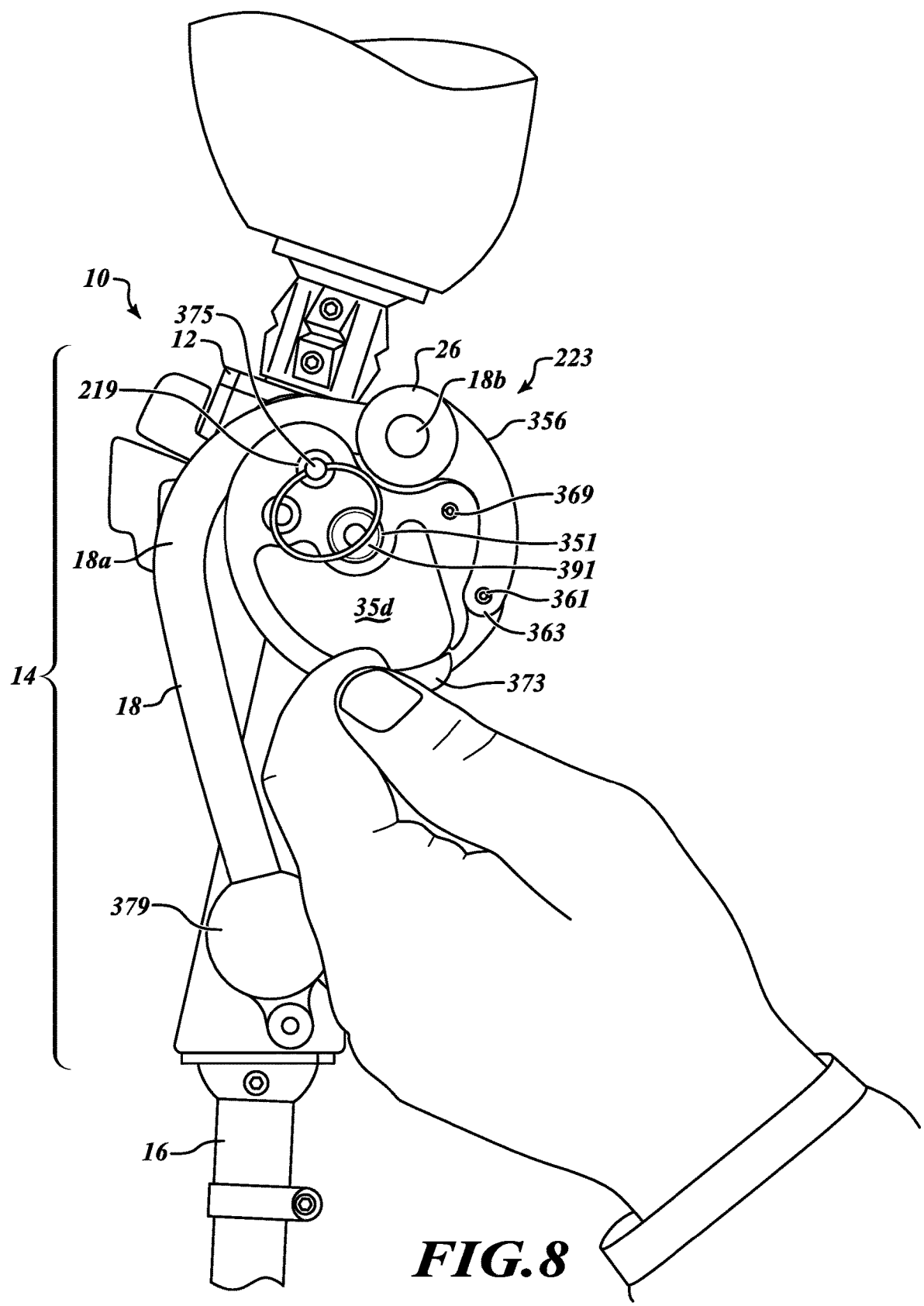
FIG. 8 is another side view of the prosthesis system shown in FIG. 1 and showing operation of the prosthesis system by a user.
Figure 10:
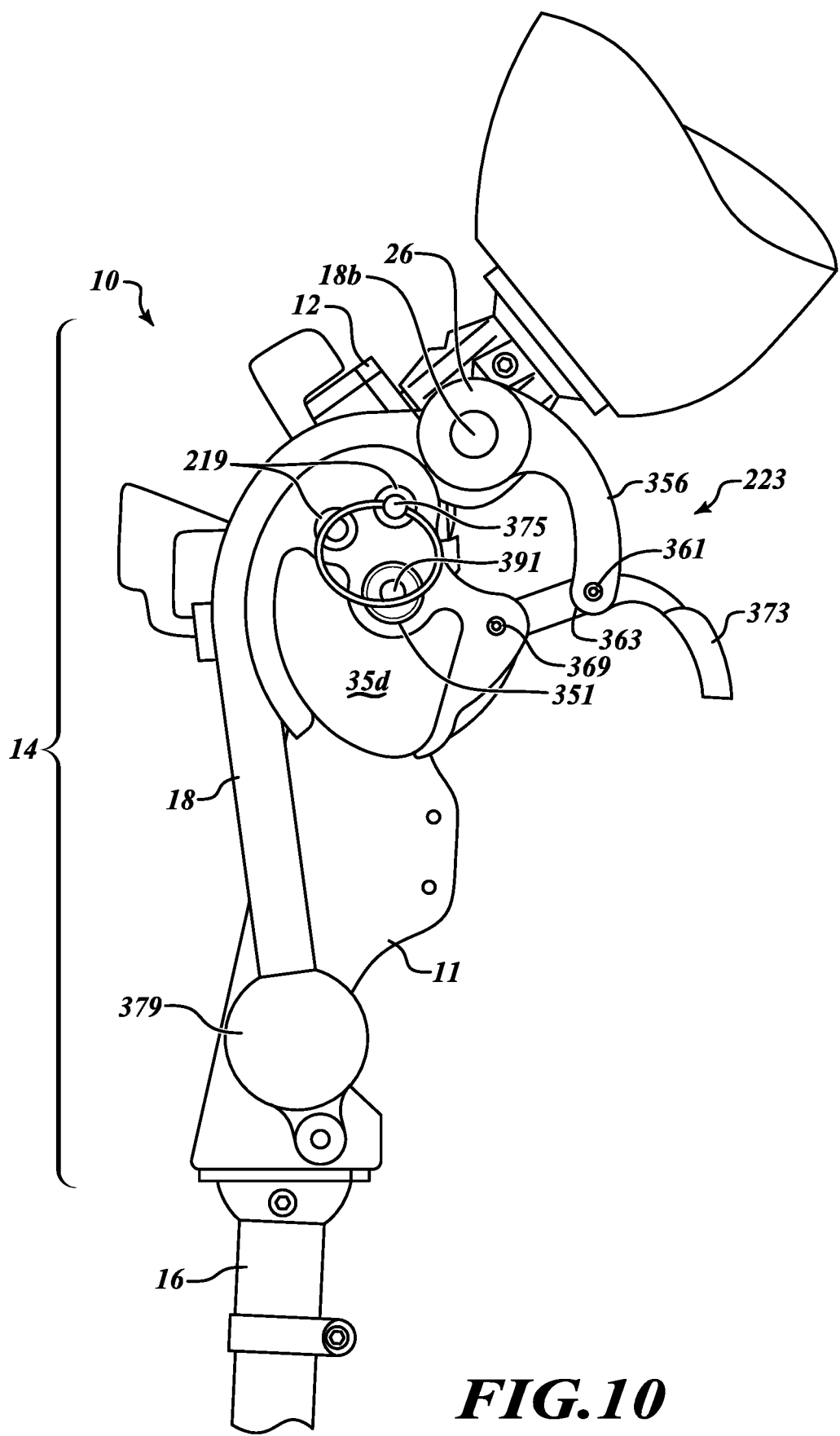
FIG. 10 is another side view of the prosthesis system shown in FIG. 1 depicted in a partially released state having the upper portion rotated relative to the lower portion thereof.
Figure 11:
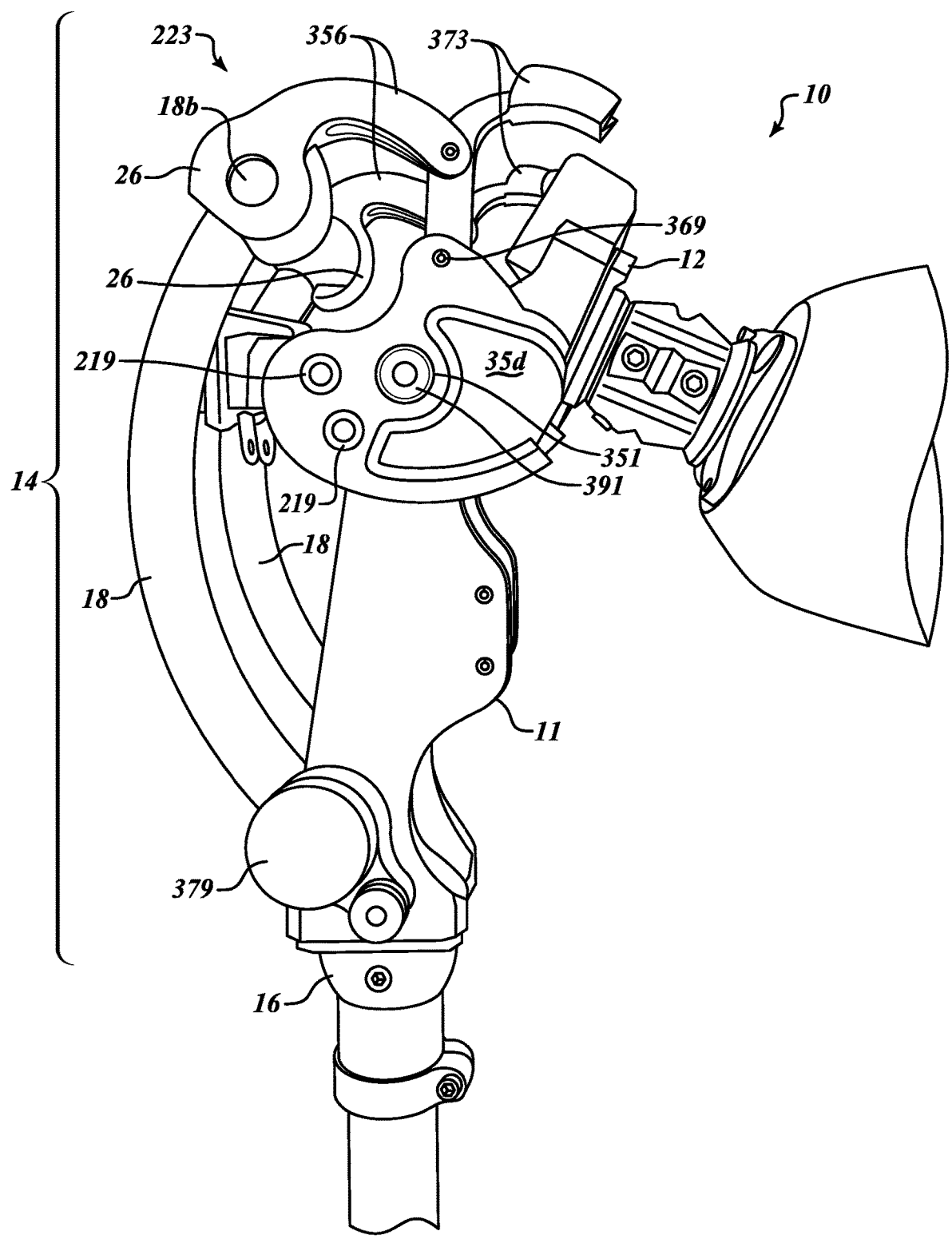
FIG. 11 is a side isometric view of the prosthesis system shown in FIG. 1 depicted in a fully released state having the upper portion rotated relative to the lower portion thereof.

Hinge 13 of self-contained joint portion 14 is coupled between proximate upper human interface portion 12 and artificial prosthetic appendage interface portion 16 that is distal from the remainder of the user's human limb through frame member 11 such that proximate human interface portion 12 and distal artificial prosthetic appendage interface portion 16 are pivotally movable with respect one to another along a pivot axis 17 between an extended straightened state (shown in FIGS. 1-6) and a retracted bent state (shown in FIGS. 7, 10, 11). For example, an axel or pivot pin 389 is provided between upper or proximate frame member 11a and distal or lower frame member 11b.

Rotatable cam member 35d provides an adjustable range of knee flexion effect. Cam member 35d includes an interior mounting aperture 351, a plurality of rotation adjustment position holes 219 formed in frame member 11. Cam member 35d is rotatably mounted to frame 11. For example, an axel or pivot pin 391 is provided between frame member 11 and interior mounting aperture 351 for rotation of cam member 35d about a pivot axis 383. Pivot axis 383 may be coincident with pivot axis 17 of frame 11 and share pivot pin 391 with hinge 13 for rotation of frame 11. Alternatively, pivot axis 383 may be parallel with and offset from pivot axis 17 of frame 11. Plurality of rotation adjustment position holes 219 (two shown) are provided through cam member 35d and each is positioned between interior mounting aperture 351 and a periphery 353 of cam member 35d. Each of rotation adjustment position holes 219 is further rotatably alignable with an interlock aperture 221 formed in frame 11. Alternatively, a single rotation adjustment position hole 219 is provided in cam member 35d and is rotatably alignable with a plurality of interlock apertures 221 formed in frame 11.

Periphery 353 of cam member 35d further includes a mid-portion retaining element 381, such as a notch or groove, substantially conforming to periphery 353 of cam member 35d. Mid-portion retaining element 381 is positioned in periphery 353 of cam member 35d between proximate retainer 26 and distal retainer 379 for supporting a portion relatively elastic portion 18a of respective elongated elastic cord member 18 between first and second end portions 18b, 18c thereof.

A pin or detent or other interlocking mechanism 375 is operable between frame 11 and the plurality of rotation adjustment position holes 219 of cam member 35d for rotationally interlocking cam member 35d into one of a plurality (two shown) of rotational .0relationships between cam member 35d and frame member 11.

At least one of elongated elastic cord members 18 includes a relatively elastic portion 18a between a relatively rigid first end portion 18b and a relatively rigid second end portion 18c and is substantially continuous therewith, wherein first end portion 18b is coupled to free end 359 of locking bar 356 positioned on periphery 353 of cam member 35d, and second end portion 18c is coupled to a second distal retainer 379 positioned on distal artificial prosthetic appendage interface portion 16.

Figure 9:
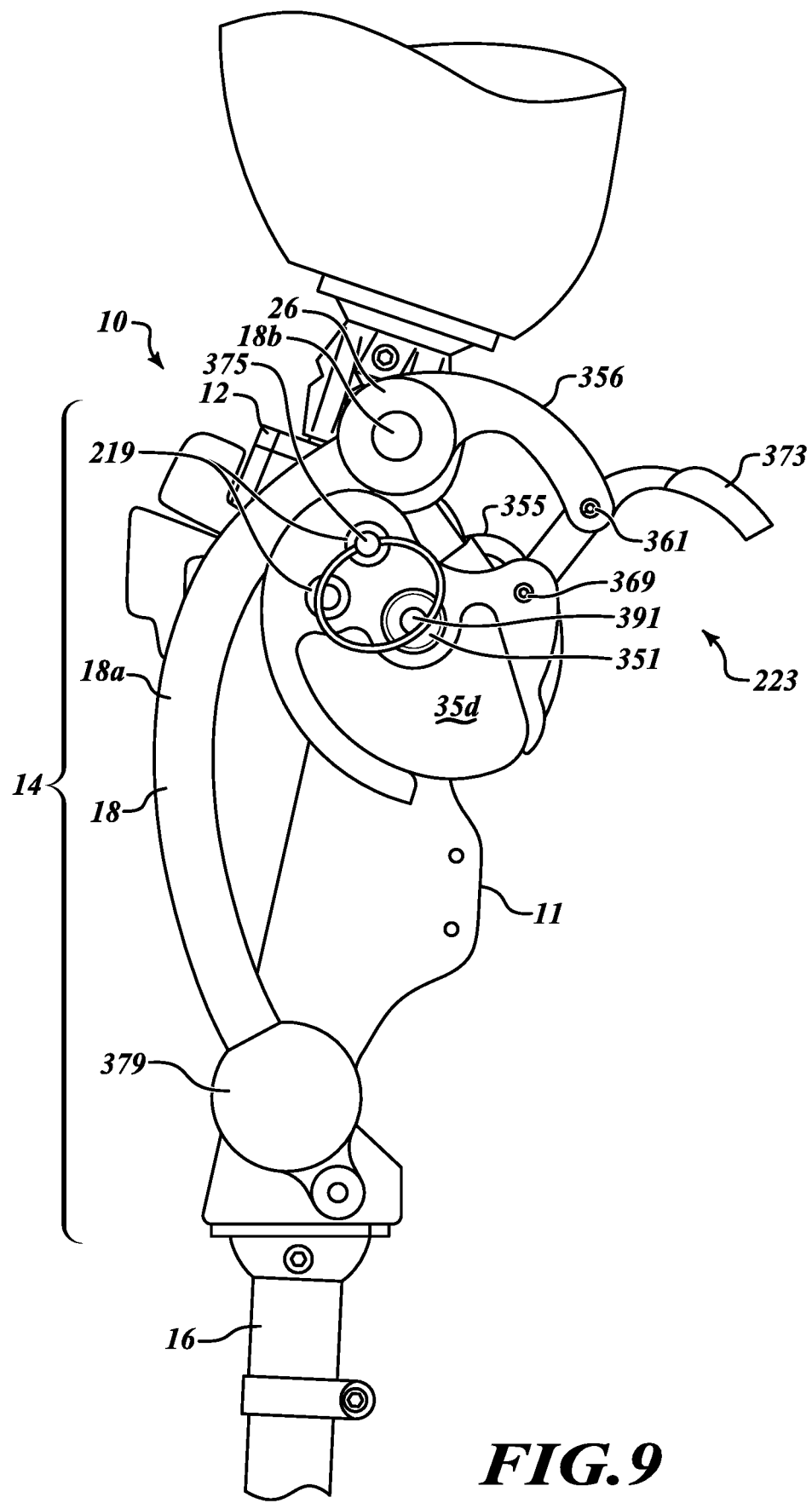
FIG. 9 is another side view of the prosthesis system shown in FIG. 1 depicted in a partially released state.

Self-contained joint portion 14 is further operable to adjust tension in elastic cord member 18. For example, a notch 355 is formed in periphery 353 of cam member 35d. A first proximate retainer 26 is structured for operating in notch 355 for retaining elongated elastic cord member 18, proximate retainer 26 includes an over-center locking mechanism or clamp 223 having a locking bar 356 with a recess 357 positioned adjacent to a free end 359 thereof and a mounting aperture 361 adjacent to a rotational end 363 thereof. A linkage 365 is rotatably coupled between mounting aperture 361 and periphery 353 of cam member 35d. A lever 367 is rotatably coupled to rotational end 363 of proximate retainer 26. A hinge 369 is positioned between a first end 371 of linkage 365 and rotational end 363 of locking bar 356, wherein lever 367 is moveable between a locked state (shown in FIGS. 1-8) and an unlocked state (shown in FIGS. 9-11) for operating linkage 365 for moving locking bar 356 between the unlocked state and the locked state. The unlocked state of locking bar 356 separates and spaces rotational end 363 thereof away from periphery 353 of cam member 35d. The locked state of locking bar 356 positions rotational end 363 thereof adjacent and in close proximity to periphery 353 of cam member 35d. An actuator 373 is coupled for operating lever 67 between the unlocked and locked states.

The unlocked state of linkage 365 provides a loose and substantially untensioned condition of elastic cord members 18, while the locked state provides an tensioned state of elastic cord members 18 that is adjustable by operation of cam member 35d by positioning one of the plurality of rotation adjustment position holes 219 relative to interlock apertures 221 and installing pin or detent or other interlocking mechanism 375 to fix rotational adjustment for a specific initial tension of elastic cord members 18. Thereafter, tension of elastic cord members 18 is increased by bending knee joint 14 about pivot axis 17.

Alternatively, when cam member 35d includes a single rotation adjustment position hole 219 with a plurality of interlock apertures 221 formed in frame 11, cam member 35d is rotatably adjusted relative to frame 11 and pin or detent or other interlocking mechanism 375 is installed to fix rotational adjustment of cam member 35d.

Optionally, a shock absorber 395 may be positioned between upper or proximate frame member 11a and distal or lower frame member 11b for cushioning the reaction to exercising of elastic cord members 18. Shock absorber 395 is offset from pivot axis 17 of frame 11. Shock absorber 395 is optionally a pneumatic cylinder and may include an adjustment mechanism 397 operable for varying the damping characteristics thereof.

What is claimed is:

1. A compact self-contained joint portion for a human prosthesis limb system, the compact self-contained joint portion comprising:

a frame comprising relatively rotatable upper and lower frame members;

an upper human interface portion coupled to the upper frame member proximate to a user and configured for coupling with a remainder of a natural human limb closer to the user's body than a previous location of a missing joint thereof;

a lower artificial prosthetic appendage interface portion coupled to the lower frame member distal from the user's body and configured for coupling with an artificial prosthetic foot or other artificial prosthetic appendage intended to replace the user's missing human limb normally residing beyond the missing joint distal from the user's body;

a hinge coupled between the relatively rotatable upper and lower frame members such that the proximate human interface portion and the distal artificial prosthetic appendage interface portion are pivotally movable with respect one to an other along a pivot axis when the relatively rotatable upper and lower frame members are rotated between a straightened state and a bent state;

a rotatable cam member having an adjustable range of knee flexion effect, the cam member comprising an interior mounting aperture structured for mounting between the proximate upper frame member and the distal lower frame member along the pivot axis;

an anti-rotation interlock mechanism operable between the cam member and the frame;

one or more elongated elastic cord members;

a first retainer structured for retaining an elongated elastic cord member relative to the cam member, wherein the first retainer couples the elastic cord member directly to the cam member; and a second retainer structured for retaining an elongated elastic cord member relative to the frame.

2. The compact self-contained joint of claim 1, wherein the rotatable cam member further comprises a retaining element structured for retaining one end of the elastic cord member directly to a periphery of the cam member.

3. The compact self-contained joint of claim 2, wherein the retaining element structured for retaining one end of the elastic cord member adjacent to a periphery of the cam member further comprises a recess formed in the periphery of the cam member; and wherein the elastic cord member terminates adjacent to the recess formed in the periphery of the cam member.

4. The compact self-contained joint of claim 1, wherein the cam member further comprises the first retainer that is structured for retaining an elongated elastic cord member relative to the cam member.

5. The compact self-contained joint of claim 4, wherein the first retainer structured for retaining an elongated elastic cord member relative to the cam member further comprises an over-center locking mechanism that is operable relative to the cam member.

6. The compact self-contained joint of claim 5, wherein the over-center locking mechanism of the first retainer further comprises the first retainer adjacent to a free end of a locking bar, a linkage that is rotatably coupled between the locking bar and the periphery of the cam member, and a lever that is rotatably coupled to locking bar for operating the linkage for moving locking bar between an unlocked state and a locked state.

7. The compact self-contained joint of claim 1, wherein each of the one or more elongated elastic cord members further comprises a relatively elastic portion between relatively rigid first and second end portions and substantially continuous therewith.

8. The compact self-contained joint of claim 1, wherein the interlock mechanism operable is further operable between the cam member and one of the upper and lower frame members.

9. A compact self-contained joint for a human prosthesis limb system, the compact self-contained joint comprising:

a frame comprising proximate and distal frame members, wherein the proximate frame member further comprises a human interface portion, and the distal frame member further comprises an artificial prosthetic appendage interface portion;

a hinge coupled between the proximate and distal frame members such that the human interface portion of the proximate frame member and the artificial prosthetic appendage interface portion of the distal frame member are relatively rotatable along a pivot axis when the proximate and distal frame members are rotated between a straightened state and a bent state;

a cam member having an adjustable range of rotation relative to the frame, the cam member comprising an interior mounting aperture structured for mounting between the proximate frame member and the distal frame member along the pivot axis and having a peripheral cam surface;

an interlock mechanism operable between the cam member and one of the proximate and distal frame members;

at least one elongated elastic cord member comprising a relatively elastic portion between relatively rigid first and second end portions and substantially continuous therewith;

a first retainer positioned on the cam member and structured for retaining one end of an elongated elastic cord member relative to the peripheral cam surface of the cam member;

a second retainer structured for retaining an elongated elastic cord member relative to the distal frame member.

10. The compact self-contained joint of claim 9, wherein the cam member is further fixable at a plurality of different relative rotational position adjustments between the cam member and the frame member within the adjustable range of rotation.

11. The compact self-contained joint of claim 10, wherein the interlock mechanism operable between the cam member and one of the proximate and distal frame members further comprises a plurality of relative rotational position adjustments between the cam member and the frame member.

12. The compact self-contained joint of claim 11, wherein the plurality of relative rotational position adjustments between the cam member and the frame member of the interlock mechanism further comprises a plurality of rotation adjustment position holes distributed between the cam member and the frame, and an interlock operable between the rotation adjustment position holes.

13. The compact self-contained joint of claim 12, wherein the interlock operable between the rotation adjustment position holes of the interlock mechanism further comprises either a pin or detent structured to operate between the plurality of rotation adjustment position holes distributed between the cam member and the frame for interlocking the cam in the plurality of relative rotational position adjustments between with the frame member.

14. The compact self-contained joint of claim 13, wherein the interlock operable between the rotation adjustment position holes of the interlock mechanism further comprises a pin that operates between the frame member and the plurality of rotation adjustment position holes for rotationally interlocking the cam member into one of the plurality of relative rotational position adjustments with the frame member.

15. The compact self-contained joint of claim 14, wherein the interlock operable between the rotation adjustment position holes of the interlock mechanism further comprises a plurality of apertures formed through the cam member and at least one aperture formed into the frame member, each of the apertures of the cam member being rotationally alignable with the aperture of the frame member.

16. The compact self-contained joint of claim 10, wherein the first retainer that is structured for retaining an elongated elastic cord member relative to the cam member further comprises:
   an over-center locking mechanism or clamp having a recess positioned adjacent to a free end of a locking bar,
   a linkage that is rotatably coupled between the locking bar and the periphery of the cam member, and
   a lever that is coupled for operating the linkage for moving the locking bar between an unlocked state and a locked state.

17. The compact self-contained joint of claim 16, wherein the peripheral cam surface of the cam member further comprises a groove formed therein that is sized to receive the relatively elastic portion of the elastic cord member between relatively rigid first and second end portions thereof.

18. A compact self-contained joint portion for a human prosthesis limb system, the compact self-contained joint portion comprising:
   a frame comprising hingably rotatable upper and lower frame members;
   an upper human interface coupled to the upper frame member proximate to a human user and configured for coupling with a remainder of the user's natural human limb closer to the user's body than a previous location of a missing joint thereof;
   a lower artificial prosthetic appendage interface coupled to the lower frame member distal from the user's body and configured for coupling with an artificial prosthetic foot or other artificial prosthetic appendage intended to replace the user's missing human limb normally residing beyond the missing joint distal from the user's body;
   a hinge coupled between the upper and lower frame members such that the proximate human interface portion and the distal artificial prosthetic appendage interface portion are rotatably movable with respect one to an other along a pivot axis when the upper and lower frame members are hingably rotated between a straightened state and a bent state;
   a cam member that is rotatable relative to one of the upper and lower frame members at least within an adjustable range of knee flexion effect, the cam member comprising an interior mounting aperture structured for mounting between the upper frame member and the lower frame member along the pivot axis, the cam member comprising a groove formed in an outer periphery thereof;
   an anti-rotation interlock mechanism operable between the cam member and the frame for interlocking the cam member in a plurality of different relative rotational positions between the cam member and the frame member;
   at least one elongated elastic cord member comprising a relatively elastic portion between relatively rigid first and second end portions and substantially continuous therewith, wherein at least the relatively elastic portion of the cord member being sized to be received into the groove formed in an outer periphery of the cam member;
   a first retainer positioned on the cam member and structured for retaining one end of an elongated elastic cord member to the cam member within the groove in the outer periphery thereof;
   a second retainer structured for retaining an elongated elastic cord member relative to the lower frame member.

19. The compact self-contained joint of claim 18, wherein the an anti-rotation interlock mechanism further comprises a plurality of rotation adjustment position holes distributed between the cam member and the frame member, and one of a pin or detent structured to operate between the plurality of rotation adjustment position holes for interlocking the cam with the frame member.

20. The compact self-contained joint of claim 18, wherein the first retainer that is structured for retaining the elongated elastic cord member within the groove in the outer periphery of the cam member further comprises:
   an over-center locking mechanism or clamp having a recess positioned adjacent to a free end of a locking bar and a mounting aperture adjacent to a rotational end thereof,
   a linkage that is rotatably coupled between the locking bar and the periphery of the cam member, and
   a lever that is rotatably coupled for operating the linkage for moving the locking bar between an unlocked state and a locked state, and
   wherein the unlocked state of the locking bar separates and spaces the rotational end thereof away from the periphery of the cam member, and the locked state of the locking bar positions the rotational end thereof adjacent to and in close proximity to the periphery of the cam member.

* * * * *